US006582719B2

(12) United States Patent
Modak et al.

(10) Patent No.: US 6,582,719 B2
(45) Date of Patent: Jun. 24, 2003

(54) COMBINATIONS OF ANTISEPTIC AND ANTIBIOTIC AGENTS THAT INHIBIT THE DEVELOPMENT OF RESISTANT MICROORGANISMS

(75) Inventors: Shanta M. Modak, River Edge, NJ (US); Suhas Tambe, New York, NY (US); Lester A. Sampath, Nyack, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 84 days.

(21) Appl. No.: 09/775,775

(22) Filed: Feb. 2, 2001

(65) Prior Publication Data

US 2002/0173775 A1 Nov. 21, 2002

(51) Int. Cl.$^7$ .............................. A61F 6/06; A61M 5/32
(52) U.S. Cl. ..................... 424/430; 424/405; 424/422; 424/614; 424/618; 424/653; 424/604; 424/205
(58) Field of Search .................................. 424/430, 422, 424/405, 614, 618, 653; 604/265

(56) References Cited

U.S. PATENT DOCUMENTS

| | | | | |
|---|---|---|---|---|
| 4,064,238 | A | | 12/1977 | Bocher et al. ............... 424/227 |
| 5,196,205 | A | | 3/1993 | Borody ........................ 424/653 |
| 5,688,516 | A | * | 11/1997 | Raad et al. .................. 424/409 |
| 5,772,640 | A | * | 6/1998 | Modak et al. ............... 604/265 |
| 5,928,671 | A | | 7/1999 | Domenico .................... 424/653 |
| 6,106,505 | A | * | 8/2000 | Modak et al. ............... 604/265 |
| 6,224,579 | B1 | * | 5/2001 | Modak et al. ............... 604/265 |

FOREIGN PATENT DOCUMENTS

WO 0057933 10/2000

OTHER PUBLICATIONS

Huang and Stewart, "Reduction of polysaccharide production in *Pseudomonas aeruginosa* biofilms by bismuth dimercaprol (BisBAL) treatment," J. Antimicrob. Chemother. 1999, 44:601–605.

Domenico et al., "Enhancement of bismuth antibacterial activity with lipophilic thiol chelators," Antimicrob Ag Chemother, 1997, 41:1697–1703.

Domenico et al., "Bismuth–dimercaprol exposes surface components of *Klebsiella pneumoniae* camouflaged by the polysaccharide capsule," Ann NY Acad Sci, 1996, 797:269–270.

Sheretz et al., "Efficacy of antibiotic–coated catheters in preventing subcutaneous *Staphylococcus aureus* infection in rabbits," J. Infect Dis, 1993, 167:98–106.

Domenico et al., "Reduction of capsular polysaccharide and potentiation of aminoglycoside inhibition in gram–negative bacteria by bismuth subsalicylate," J. Antimicrob., 1991, 28:801–810.

Bierer, "Bismuth subsalicylate: history, chemistry, and safety." Rev. Inf. Dis., 1990, 12 Suppl 1:S3–S8.

Leon–Barau et al., "In vitro and in vivo effects of three bismuth compounds in fermentation by colonic bacteria," Rev. Inf. Dis., 1990, 12 Suppl 1:S24–S29.

Goodman and Gilman's The Pharmacological Basis of Therapeutics, Gilman et al., editors, Seventh Edition, 1985, Macmillan Publishing Company, New York, pp. 959–960, 1066–1067, 1171.

* cited by examiner

*Primary Examiner*—Jyothsan Venkat

(57) ABSTRACT

The present invention relates to compositions comprising a combination of one or more antiseptic and an antibiotic. It is based, at least in part, on the discovery that such combinations tend to deter the formation of antibiotic-resistant organisms. In preferred, nonlimiting embodiments of the invention, the antibiotic is minocycline and the antiseptic is a chlorhexidine compound, triclosan, or benzalkonium chloride, and in particular embodiments, a silver salt or a bismuth salt is added. Examples of specific, nonlimiting embodiments of the invention include combinations of (i) minocycline, triclosan, and a bismuth salt; (ii) minocycline, a chlorhexidine compound, and a bismuth salt; and (iii) minocycline, benzalkonium chloride, and a bismuth salt. The present invention further provides for articles, such as, but not limited to, medical articles, which have been treated with or which otherwise comprise a combination of antiseptic and antibiotic.

15 Claims, No Drawings

COMBINATIONS OF ANTISEPTIC AND ANTIBIOTIC AGENTS THAT INHIBIT THE DEVELOPMENT OF RESISTANT MICROORGANISMS

1. INTRODUCTION

The present invention relates to combinations of antiseptic and antibiotic agents which exert an antimicrobial effect while deterring, relative to other antimicrobial agents, the development of antibiotic-resistant microorganisms.

2. BACKGROUND OF THE INVENTION

An antiseptic is a substance that kills or prevents the growth of microorganisms, and which is typically applied to living tissue, distinguishing the class from disinfectants, which are usually applied to inanimate objects (Goodman and Gilman's "*The Pharmacological Basis of Therapeutics*", Seventh Edition, Gilman et al., editors, 1985, Macmillan Publishing Co., (hereafter, Goodman and Gilman") pp. 959–960). Common examples of antiseptics are ethyl alcohol and tincture of iodine. Alcohol is usually used to clean a subject's skin prior to insertion of a hypodermic needle; tincture of iodine is frequently applied as a first step in wound care, both uses intended to decrease the number of microbes on the skin to prevent invention.

While antiseptics once played a more substantial role in wound management, they are now secondary in importance to antibiotics, chemical substances produced by various species of microorganisms (or synthetic or semisynthetic analogs thereof) that kill or suppress the growth of other microorganisms (Goodman and Gilman, p. 1067). Antibiotics may be administered systemically or locally applied. Since the production of penicillin in 1941, antibiotics have been widely used, with the result that microorganism strains have developed which are resistant to one or more antibiotic. The generation of resistant organisms has created an ever-increasing need for the identification or synthesis of new antibiotics (Goodman and Gilman, p. 1066).

One particularly useful class of antibiotics is tetracyclines, which exert their antibacterial action by binding to microbial ribosomes and preventing protein synthesis (Goodman and Gilman, p.1171). Tetracyclines are primarily bacteriostatic when tested in vitro, and only multiplying microorganisms are affected. They possess antimicrobial activity against a wide variety of microorganisms, including gram-positive and gram negative bacteria, and against some microorganisms, such as Rickettsiae, Mycoplasma, Chlamydia, some atypical Mycobacteria, and ameobae, that are resistant to other classes of antibiotics (Id.). Minocycline, doxycycline, tetracycline and oxytetracycline are tetracycline-class drugs listed in order of decreasing antimicrobial activity (Id.).

The first documented medical use of bismuth occurred in 1773, when it was used in salves. Since then it has been used to combat diarrhea, gastroenteritis, stomach cramps, vomiting and ulcers. It has been used for the treatment of surgical wounds (Bierer, 1990, Rev. Infect. Dis. 12 (Suppl. 1): S3–S8). The antimicrobial effect of bismuth is well known. The reducing effect of bismuth compounds on fermentation by colonic bacteria has been demonstrated both in vitro and in vivo (Leon-Barua et al., 1990, Rev. Infect. Dis. 12 (Suppl. 1): S24–S29).

Bismuth salts have also been shown to have a significant effect on the inhibitory activity of antibiotics. Bismuth salicylate ("BSS") and bismuth nitrate have been reported to potentiate aminoglycoside activity against gram negative bacteria (Domenico et al., 1991, J. Antimicrob. Chemother. 28:801–810). BSS, bismuth nitrate and bismuth dimercaprol (Bis-BAL), have also been reported to inhibit capsular polysaccharide production by the bacterium *Klebsiella pneumoniae* (Domenico et al., 1991, J. Antimicrobial Chemother. 28:801–810; Domenico et al., 1996, Ann. N. Y. Acad. Sci. 797:269–270). BisBAL has also been shown to have good activity against a wide spectrum of bacteria among the genera Yersinia, Shigella, Salmonella, Pseudomonas, Proteus, Enterobacter, Escherichia, Staphylococci, Helicobacter, and Clostridia (Domenico, 1997, Antimicrob. Ag. Chemother. 41:1697–1703) and to inhibit polysaccharide production in biofilms (Huang and Stewart, 1999, J. Antimicrob. Chemother. 44:601–605). The use of bismuth salts in combination with thiol compounds for the preparation of a composition with anti-infective properties has been described by Domenico, 1999, U.S. Pat. No. 5,928,671. The potentiation of antibiotics by a bismuth salt of pyrrolidone carboxylic acid, resulting in higher tissue levels of the antibiotic was described by Bocher et al., 1977, U.S. Pat. No. 4,064,238. The use of bismuth salts, in combination with an antibiotic and metronidazole for the eradication of *Helicobacter pylori*, a causative agent of duodenal ulcer, has also been described (Borody, 1993, U.S. Pat. No. 5,196,205).

International Application No. PCT/US00/08692, entitled "TRICLOSAN AND SILVER COMPOUND CONTAINING MEDICAL DEVICES" by The Trustees of Columbia University in the City of New York teaches the addition of various antibiotics, including those set forth herein, to combinations of triclosan and silver salts. The use of bismuth salts, as set forth herein, was not disclosed.

3. SUMMARY OF THE INVENTION

The present invention relates to compositions comprising a combination of one or more antiseptic and an antibiotic. It is based, at least in part, on the discovery that such combinations tend to deter the formation of antibiotic-resistant organisms. In preferred, nonlimiting embodiments of the invention, the antibiotic is minocycline and the antiseptic is a chlorhexidine compound, triclosan, or benzalkonium chloride, and in particular embodiments, a silver salt or a bismuth salt is added. Examples of specific, nonlimiting embodiments of the invention include combinations of (i) minocycline, triclosan, and a bismuth salt; (ii) minocycline, a chlorhexidine compound, and a bismuth salt; and (iii) minocycline, benzalkonium chloride, and a bismuth salt. The present invention further provides for articles, such as, but not limited to, medical articles, which have been treated with or which otherwise comprise a combination of antiseptic and antibiotic.

Antibiotics, unlike antiseptics, may be used in relatively high concentrations because they tend to be less toxic to host tissue. The use of higher concentrations may result in longer term efficacy. In contrast, antiseptics typically should be used in lower concentrations, because they are frequently toxic to host tissue. Even at lower concentrations, however, antiseptics may provide cidal action against a wide range of microorganisms. Thus, combinations of antibiotics and antiseptics according to the invention may provide for prolonged antimicrobial effectiveness against a variety of microbes.

4. DETAILED DESCRIPTION OF THE INVENTION

The present invention relates to compositions comprising combinations of (i) an antibiotic selected from the group consisting of minocycline, rifampin, and norfloxacin; and (ii) an antiseptic selected from the group consisting of biguanide compounds, triclosan, and benzalkonium chloride. In preferred embodiments, such compositions further comprise a salt of bismuth, cerium, or zinc or a silver-containing compound. Such compositions may be incorporated into or onto medical devices to impart antimicrobial activity to the devices. The present invention also provides for methods of using such compositions in the preparation of medical devices.

Biguanide compounds which may be used according to the invention include poly (hexamethylene biguanide) hydrochloride and chlorhexidine compounds. Chlorhexidine is the term denoting the chemical compound 1,6 bis($N^5$-p-chlorophenyl-$N^1$-biguanido)hexane). Chlorhexidine compounds include chlorhexidine free base ("CHX") as well as chlorhexidine salts, such as chlorhexidine diphosphanilate, chlorhexidine digluconate ("CHG"), chlorhexidine diacetate ("CHA"), chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-α-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynapthoate, and chlorhexidine embonate.

Bismuth salts which may be used according to the invention include bismuth nitrate, bismuth citrate, bismuth salicylate, bismuth borate, bismuth mandelate, bismuth palmitate, bismuth benzoate, and bismuth sulfadiazine.

Cerium salts which may be used according to the invention include cerium nitrate and other cerium salts having a water solubility similar to cerium nitrate.

The term silver-containing compound, as used herein, refers to a compound comprising silver, either in the form of a silver atom or a silver ion unlinked or linked to another molecule via a covalent or noncovalent (e.g., ionic) linkage, including but not limited to covalent compounds such as silver sulfadiazine ("AgSD") and silver salts such as silver oxide ("$Ag_2O$"), silver carbonate ("$Ag_2CO_3$"), silver deoxycholate, silver salicylate, silver iodide, silver nitrate ("$AgNO_3$"), silver paraaminobenzoate, silver paraaminosalicylate, silver acetylsalicylate, silver ethylenediaminetetraacetic acid ("Ag EDTA"), silver picrate, silver protein, silver citrate, silver lactate and silver laurate.

Zinc salts which may be used according to the invention include zinc acetate and other zinc salts having a water solubility similar to zinc acetate.

The present invention provides for the incorporation of combinations of the foregoing elements into or onto medical devices, and for the medical devices which incorporate said combinations. The terms "medical article" and "medical device" are used interchangeably herein. Medical articles that may be treated according to the invention are either fabricated from or coated or treated with biomedical polymer (and hence may be referred to as "polymer-containing medical articles") and include, but are not limited to, catheters including urinary catheters and vascular catheters (e.g., peripheral and central vascular catheters), wound drainage tubes, arterial grafts, soft tissue patches (such as polytetrafluoroethylene ("PTFE") soft tissue patches), gloves, shunts, stents, tracheal catheters, wound dressings, sutures, guide wires and prosthetic devices (e.g., heart valves and LVADs). Vascular catheters which may be prepared according to the present invention include, but are not limited to, single and multiple lumen central venous catheters, peripherally inserted central venous catheters, emergency infusion catheters, percutaneous sheath introducer systems and thermodilution catheters, including the hubs and ports of such vascular catheters.

In particular embodiments, the combinations of the invention may be incorporated into or onto a medical device by exposing the device to a treatment solution comprising the combination in an appropriate solvent system. Said treatment solutions fall within the scope of compositions covered by the present invention. Where the treatment solution contains minocycline, the concentration of minocycline is between 1 and 8 percent weight/volume (w/v), and preferably between 3 and 5 percent (w/v); where the treatment solution contains rifampin, the concentration of rifampin is between 1 and 8 percent (w/v), and preferably between 3 and 5 percent (w/v); where the treatment solution contains norfloxacin, the concentration of norfloxacin is between 1 and 8 percent (w/v) and preferably between 3 and 5 percent (w/v); where the solution contains a chlorhexidine compound, the concentration of chlorhexidine compound is between 1 and 8 percent (w/v) and preferably between 3 and 5 percent (w/v); where the treatment solution contains triclosan, the concentration is between 1 and 8 percent (w/v) and preferably between 3 and 5 percent (w/v); where the treatment solution contains benzalkonium chloride, the concentration of benzalkonium chloride ("BZK") is between 0.25 and 1 percent (w/v) and preferably is 0.5 percent (w/v); where the treatment solution contains a bismuth salt, the concentration of bismuth salt is between 0.5 and 2 percent (w/v) and preferably is 2 percent (w/v); where the treatment solution contains a cerium salt, the concentration of cerium salt is preferably between 1 and 5 percent (w/v); where the treatment solution contains a zinc salt, the concentration of zinc salt is between 1 and 5 percent (w/v) and preferably is 2 percent (w/v); and where the treatment solution contains a silver-containing compound, the concentration of silver-containing compound is between 0.5 and 2 percent (w/v) and preferably is 1 percent. The above ranges, e.g. "between X percent and Y percent", include the boundary values X and Y and are intended herein to encompass variations of 20 percent of the value of X and Y, in other words, the ranges should be interpreted to mean "between X±0.20X and Y±0.20Y".

An appropriate solvent system is a solvent system which will either solubilize or, less desirably, produce a suspension of anti-infective agents, which will preferably result in slight swelling of the medical device (to facilitate incorporation of anti-infective agents), but which will preferably not substantially alter the surface of the medical device (e.g., render the surface rough) so as not to impair the clinical usefulness of the device. Specific non-limiting examples of solvent systems include 70 percent (volume/volume; "v/v") tetrahydrofuran ("THF") and 30 percent (v/v) methanol ("MeOH"), and more preferably, for dissolving an antibiotic, 50 percent (v/v) tetrahydrofuran ("THF") and 50 percent (v/v) methanol. Such treatment solutions may further comprise a biomedical polymer. As specific, non-limiting examples, the treatment solution may comprise 3 percent (w/v) 93A polyurethane and 1 percent (w/v) 60D polyurethane or 1 percent (w/v) 93A polyurethane and 3 percent (w/v) 60D polyurethane.

For example, a polyurethane catheter may be exposed to a treatment solution of the invention (by dipping and/or drawing treatment solution through the catheter lumen) for between 2 and 200 seconds, and preferably between 2 and 100 seconds, and then dried at room temperature. A polyurethane catheter treated in this manner using 1:1 THF/MeOH as a solvent system would contain the following amounts of anti-infective substances (where the term "anti-infective" refers to antibiotics and antiseptics): where the catheter contains contains minocycline, the amount of minocycline is between 100 and 450 micrograms per centimeter; where the catheter contains rifampin, the amount of rifampin is between 100 and 450 micrograms per centimeter; where the catheter contains norfloxacin, the amount of norfloxacin is between 100 and 450 micrograms per centimeter; where the catheter contains a chlorhexidine compound, the amount of chlorhexidine compound is between 130 and 520 micrograms per centimeter; where the catheter contains triclosan, the amount is between 130 and 750 micrograms per centimeter; where the catheter contains benzalkonium chloride, the amount of benzalkonium chloride ("BZK") is between 25 and 100 micrograms per centimeter; where the catheter contains a bismuth salt, the amount of bismuth salt is between 50 and 300 micrograms per centimeter; where the catheter contains a cerium salt, the amount of cerium salt is between 50 and 200 micrograms per centimeter; where the catheter contains a zinc salt, the amount of zinc salt is between 50 and 200 micrograms per centimeter; and where the catheter contains a silver-containing compound, the amount of silver-containing compound is between 25 and 300 micrograms per centimeter. Furthermore, the present invention provides for catheters and other medical devices comprising the abovementioned amounts of anti-infective agents in the inventive combinations whether they have been prepared using such a treatment solution or by other means, such as by extrusion, by "painting" a coating solution comprising the inventive combinations, by coating with a powder comprising the inventive combinations, etc.

Examples of combinations covered by the present invention include, but are not limited to, the following:
 minocycline and bismuth;
 minocycline and chlorhexidine free base;
 minocycline and chlorhexidine diacetate;
 minocycline and chlorhexidine digluconate;
 minocycline and triclosan;
 minocycline, chlorhexidine free base and bismuth nitrate;
 minocycline, chlorhexidine diacetate, and bismuth nitrate;
 minocycline, chlorhexidine digluconate, and bismuth nitrate;
 minocycline, triclosan and bismuth nitrate;
 minocycline, chlorhexidine free base, and benzalkonium chloride;
 minocycline, chlorhexidine diacetate and benzalkonium chloride;
 minocycline, chlorhexidine digluconate and benzalkonium chloride;
 minocycline, triclosan and benzalkonium chloride;
 minocycline, chlorhexidine free base, and benzalkonium chloride;
 minocycline, chlorhexidine diacetate and benzalkonium chloride;
 minocycline, chlorhexidine digluconate and benzalkonium chloride;
 minocycline, triclosan and benzalkonium chloride;
 minocycline, chlorhexidine free base, bismuth nitrate and benzalkonium chloride;
 minocycline, chlorhexidine diacetate, bismuth nitrate and benzalkonium chloride;
 minocycline, triclosan and silver carbonate;
 minocycline, chlorhexidine digluconate, bismuth nitrate and benzalkonium chloride; and
 minocycline, triclosan, bismuth nitrate and benzalkonium chloride.

5. WORKING EXAMPLES 5.1. Example

Reduced Efficacy of Catheters Containing Antibiotics Against Antibiotics-resistance Bacteria Recently catheters impregnated with a combination of two antibiotics, minocycline and rifampin, have been developed for clinical use. It was believed that development of resistance to these agents used in combination would be unlikely since each agent has a different mode of action, such that they might act synergistically. However, studies in which the catheters have been implanted into rats have shown that, over time, the catheters lose antimicrobial activity against bacterial strains exhibiting either low level resistance to this antibiotic combination or high level resistance to rifampin. In contrast, catheters impregnated with the antiseptics chlorhexidine and silver sulfadiazine were effective against these antibiotic resistant strains.

To describe these studies in greater detail, intravenous catheters treated with minocycline and rifampin ("MR") or chlorhexidine and silver sulfadiazine ("AST") were prepared as follows. MR polyurethane catheters were purchased from Cook Critical Care, Inc., and contain approximately 0.5 mg of minocycline and 0.5 mg of rifampin per centimeter. To prepare the AST catheters, polyurethane catheters were dipped in a treatment solution comprising 3 percent (w/v) chlorhexidine diacetate ("CHA"), 0.75 percent (w/v) silver sulfadiazine ("AgSD"), 3 percent (w/v) 93A polyurethane and 1 percent (w/v) 60D polyurethane, in a solvent system consisting of 70 percent (v/v) tetrahydrofuran and 30 percent (v/v) methanol at room temperature for 2–5 seconds.

Rats received subcutaneous implants of MR or AST catheter segments. At 7, 14, and 21 days post-implant, catheter segments were removed and then placed on agar plates seeded with either a parent *Staphylococcus epidermidis* strain ("S. epi-s"; ATCC Acc. No. 35983) or a rifampin resistant variant thereof ("R-r") or a strain resistant to both minocycline and rifampin ("MR-r"). The zones of inhibition against these strains produced by the MR or AST catheter segments were measured, and the results are shown in Table I.

TABLE I

Effectiveness of Antimicrobial Catheters Against Sensitive and Resistant Bacterial Strains
Zones of inhibition (mm)

| STRAIN | INITIAL | | DAY 7 | | DAY 14 | | DAY 21 | |
| --- | --- | --- | --- | --- | --- | --- | --- | --- |
|  | MR | AST | MR | AST | MR | AST | MR | AST |
| S.epi-s | 24 | 14 | 23 | 9 | 22.5 | 8 | 17.9 | 7.3 |
| MR-r | 22.3 | 14 | 21 | 9 | 14 | 8 | 10 | 7.5 |
| R-r | 21 | 13.3 | 9 | 9 | 7 | 8 | 6.8 | 7.8 |

To summarize, by day 7 the MR catheter's activity against the R-r strain was greatly reduced. At days 7 and 14 the zones of inhibition against both the MR-r and R-r strains were drastically reduced compared to those against the parent, non-resistant *S. epidermidis* strain. The activity of the AST catheters was unaffected regardless of the antibiotic resistance profile of the test organisms.

5.2. Example

Efficacy of Antibiotic/Antiseptic Combinations

Minimum inhibitory concentration ("MIC"): The MIC of each antimicrobial agent, singly and in combination, was determined using a liquid medium, namely Trypticase Soy Broth ("TSB"). The antimicrobial agents were serially diluted so that each tube contained 5 ml which was then inoculated with microbes at a concentration of either $10^4$ or $10^6$ colony forming unit ("cfu") per milliliter. These levels of inoculum represent a low and mid-level range of numbers of organisms which may potentially colonize IV catheters. Tubes were incubated for 24 hours at 37° C. and checked for turbidity. The lowest concentration of drug with no visible turbidity was deemed the MIC.

Development of Resistance: *S. epidermidis* was evaluated in conjunction with various antimicrobial agents and combinations for the development of resistant organisms. Culture tubes containing 5 ml of TSB were inoculated to obtain approximately $1 \times 10^4$ organisms per milliliter at drug concentrations ranging from 3 doubling dilutions above to 3 doubling dilutions below the MIC for each agent. The initial inoculum was prepared by growing the culture in TSB overnight. Tubes were incubated at 37° C. for 24 hours. The culture tube serially preceding the MIC-containing tube was diluted to $10^5$ cfu/ml and used for the next transfer. After 10 to 20 passages cultures below the MIC tube were subcultured on blood agar plates and stored for susceptibility tests. This experiment was repeated using a cell density of $10^6$ cfu/ml at every passage. The following antiseptics and antibiotics were tested singly and in combination for resistance development using the above test: chlorhexidine diacetate ("CHX"), triclosan ("T"), parachlorometaxylenol ("PCMX"), polyhexamethylenebiguanide ("PHMB"), minocycline ("M"), tobramycin ("Tb"), norfloxacin ("Nf"), minocycline and rifampin ("M+R"), chlorhexidine and norfloxacin ("CHX+Nf"), chlorhexidine and tobramycin ("CHX+Tb"), triclosan and minocycline ("T+M"), minocycline and parachlorometaxylenol ("PCMX+M"), polyhexamethylenebiguanide and minocycline ("PHMB+M"), and chlorhexidine and rifampin ("CHX+R"). The results of thee studies are presented in Tables IIA, IIB and III.

TABLE IIA

MICs of Antibiotic and Antiseptic
Before and After 10–20 Passages Through
Subinhibitory Concentrations Using an Inoculum Density of $10^4$ cfu/ml

| | MIC (μg/ml) BEFORE PASSAGE | MIC (μg/ml) AFTER PASSAGE | INCREASE IN MIC (fold) |
|---|---|---|---|
| ANTIBIOTIC | | | |
| Minocycline (M) | 0.078 | 0.156 | 2 |
| Rifampin (R) | 0.0195 | 500 | 25,000 |
| Norfloxacin (Nf) | 0.05 | 2.0 | 40 |
| Tobramycin (Tb) | 0.025 | 0.5 | 20 |
| ANTISEPTIC | | | |
| Chlorhexidine (CHX) | 0.5 | 1.0 | 2 |
| Triclosan (T) | 0.35 | 2.5 | 7 |
| PHMB | 0.31 | 0.31 | 1.0 |

TABLE IIA-continued

MICs of Antibiotic and Antiseptic
Before and After 10–20 Passages Through
Subinhibitory Concentrations Using an Inoculum Density of $10^4$ cfu/ml

| | MIC (μg/ml) BEFORE PASSAGE | MIC (μg/ml) AFTER PASSAGE | INCREASE IN MIC (fold) |
|---|---|---|---|
| PCMX | 125 | 125 | 1.0 |
| ANTIBIOTIC COMBINATION | | | |
| M + R (1:1)* | 0.019 | 0.31 | 16 |
| ANTISEPTIC ANTIBIOTIC COMBINATION | | | |
| CHX + M (1:1)* | 0.06 | 0.1 | 1.66 |
| CHX + R (3:1)* | 0.06 | 0.5 | 8.3 |
| CHX + NF (1:1)* | 0.015 | 0.015 | 1.0 |
| T + M (1:1)* | 0.0125 | 0.0125 | 1.0 |
| T + M (1.6:1)* | 0.0125 | 0.0125 | 1.0 |
| PHMB + M (1:1)* | 0.1 | 0.1 | 1.0 |
| PHMB + TB (1:1)* | 0.1 | 0.2 | 2.0 |

*w/w

TABLE IIB

MIC (μg/ml) Initially and After 10 Transfers Through
Subinhibitory Concentrations Using An Inoculumn Density
of $10^6$ cfu/ml

| GROUP | MIC (cfu/ml) BEFORE PASSAGE | MIC (cfu/ml) AFTER PASSAGE | INCREASE IN MIC (fold) |
|---|---|---|---|
| Minocycline | 0.125 | 0.5 | 4 |
| Triclosan | 0.45 | 3.2 | 7 |
| M + T (1:1)* | 0.0125 | 0.0125 | 1 |
| M + R (1:1)* | 0.06 | 1.0 | 17 |

*w/w

Of all the antibiotics tested, minocycline appears to be less likely to develop resistant bacteria against lower challenges ($10^4$ cfu/ml). However, at higher cell densities, the MIC of minocycline increased 4-fold. Combinations of antiseptics such as triclosan and antibiotics such as minocycline appear to prevent the development of minocycline resistant bacteria.

TABLE III

Synergistic Activity of Antibiotics and Antiseptics,
Inoculum of $10^4$ cfu/ml

| COMPOUND | MIC (μg/ml) | FRACTIONAL INHIBITORY CONCENTRATION |
|---|---|---|
| Triclosan | 0.35 | N.A. |
| Minocycline | 0.078 | N.A. |
| Triclosan + Minocycline (1:1)* | 0.015 + 0.015 | 0.235 |
| Triclosan + Minocycline (1.6:1)* | 0.0077 + 0.0048 | 0.0835 |
| Chlorhexidine | 0.5 | N.A. |
| Norfloxacin | 0.05 | N.A. |
| Chlorhexidine + Norfloxacin (1:1)* | 0.015 | 0.165 |

*w/w.

The concentration of each agent in Table III in the combination is expressed as a fraction of the concentration that causes the same effect when the same agent is tested alone (i.e., its fractional inhibitory concentration). If the sum of the fractional inhibitory concentrations is less than one, then the combination is synergistic.

In conclusion, norfloxacin and minocycline were observed to exhibit synergy in combination with, respectively, chlorhexidine and triclosan, in addition to having lower increases in MIC after 20 passages through sub-inhibitory concentrations in vitro (see Table IIA).

5.3 Example

Antiseptic/Antibiotic-treated Catheters

Method. Polyurethane catheter segments were treated with one of the following:

5 percent (w/v) tobramycin was suspended in 50 percent (v/v) methanol and 50 percent (v/v) tetrahydrofuran (THF) with 3 percent (w/v) 60D polyurethane and 1 percent (w/v) 93A polyurethane;

5 percent (w/v) norfloxacin was suspended in 50 percent (v/v) methanol and 50 percent (v/v) THF with 3 percent (w/v) 60D polyurethane and 1 percent (w/v) 93A polyurethane;

or 5 percent (w/v) minocycline was dissolved in 50 percent (v/v) methanol and 50 percent (v/v) THF with 3 percent (w/v) 60D polyurethane and 1 percent (w/v) 93A polyurethane Treatment consisted of exposing the catheter segment to treatment solution for 2–5 seconds at room temperature, and then air-drying the segments. Then, 0.5 cm catheter segments were placed vertically on trypticase soy agar ("TSA") plates seeded with 0.3 ml of $10^8$ cfu/ml of a test culture of *Staphylococcus epidermidis*. After incubation at 37° C. for 24 hours the zones of inhibition were measured, after which the catheter segments were transferred to fresh TSA plates seeded with the same culture. Transfers were done every 24 hours during the study.

Results. Results are presented in Table IV.

TABLE IV

| | Zones of Inhibition (mm) | | |
|---|---|---|---|
| CATHETER GROUP | DAY 1 | DAY 4 | DAY 7 |
| Tobramycin | >25 | 7 | 0 |
| Norfloxacin | >25 | 10 | 8 |
| Minocycline | >25 | 26 | 15 |

Zone sizes smaller than 15 mm indicate that the treatment with antibiotic may not be effective in preventing *S. epidermidis* adherence to catheters (Sheretz et al., 1993, J. Infect. Dis. 167:98–106).

Discussion. Based on the data presented in Tables IIA, IIB and III, norfloxacin, tobramycin, and minocycline, in combination with chlorhexidine or triclosan, appear to have the lowest increase in MIC after 20 transfers through sub-inhibitory concentrations of drugs. However, in order for antimicrobial activity of a medical device to be effective for an extended period of time, an incorporated antibiotic and/or antiseptic should be released slowly and steadily. The data presented in Table IV suggests that for catheters, the choice of antibiotics for incorporation should be limited to minocycline and rifampin, because the antibiotics norfloxacin and tobramycin diffuse out of a catheter in a day or two, whereas minocycline and rifampin are released at a slower rate over a longer period of time. Further, norfloxacin and tobramycin have disadvantageous solubility characteristics, having limited solubility in the tetrahydrofuran/methanol solvent systems used to impregnate polyurethane catheters. This low solubility results in an upper limit of norfloxacin or tobramycin incorporated of about 0.5 percent (w/v), a level associated with short-lived, low antimicrobial activity (zones of inhibition smaller than 10 mm, lasting for 1–2 days). Treatment of catheters with suspensions containing 5 percent (w/v) of norfloxacin or tobramycin resulted in a very rough catheter surface, such that while the antimicrobial activity may be increased, the catheters cannot be used clinically. Only minocycline has been found to be usable at high concentrations which achieve long-term antimicrobial activity without compromising catheter surface smoothness.

5.4 Example

Rifampin or Minocycline Plus Antiseptics

Method. Polyurethane catheter segments were treated with one of the following:

5 percent (w/v) chlorhexidine free base and 1 percent (w/v) rifampin in 50 percent (v/v) methanol and 50 percent (v/v) THF with 3 percent (w/v) 60D polyurethane and 1 percent (w/v) 93A polyurethane;

5 percent (w/v) chlorhexidine diacetate and 1 percent (w/v) minocycline in 50 percent (v/v) methanol and 50 percent (v/v) THF with 3 percent (w/v) 60D polyurethane and 1 percent (w/v) 93A polyurethane;

3 percent (w/v) chlorhexidine diacetate and 3 percent (w/v) minocycline in 50 percent (v/v) methanol and 50 percent (v/v) THF with 3 percent (w/v) 60D polyurethane and 1 percent (w/v) 93A polyurethane;

5 percent (w/v) triclosan and 3 percent (w/v) rifampin in 50 percent (v/v) methanol and 50 percent (v/v) THF with 3 percent (w/v) 60D polyurethane and 1 percent (w/v) 93A polyurethane; or 5 percent (w/v) triclosan and 3 percent (w/v) minocycline in 50 percent (v/v) methanol and 50 percent (v/v) THF with 3 percent (w/v) 60D polyurethane and 1 percent (w/v) 93A polyurethane.

Treatment consisted of exposing the catheter segment to treatment solution for 2–5 seconds at room temperature, and then drying the segments in air. Then, 0.5 cm catheter segments were placed vertically on trypticase soy agar ("TSA") plates seeded with 0.3 ml of $10^8$ cfu/ml of a test culture of either (i) rifampin resistant *S. epidermidis;* (ii) minocycline passaged *S. epidermidis* (where the MIC of minocycline did not change); or (iii) *S. epidermidis* sensitive to minocycline and rifampin. After incubation at 37° C. for 24 hours the zones of inhibition were measured.

Results. The experiments described in the preceding paragraph produced the results shown in Table V.

TABLE V

| | Zones of Inhibition (mm) | | |
|---|---|---|---|
| CATHETER GROUP | Rifampin Resistant *S. epidermidis* | Minocycline Passaged *s. epidermidis* | Minocycline and Rifampin Resistant *S. epidermidis* |
| 5% Chlorhexidine + 1% Rifampin | 11 | 21 | 21 |
| 5% Chlorhexidine + 1% Minocycline | 19 | 20 | 20 |
| 3% Chlorhexidine + 3% Minocycline | 20 | 20 | 20 |

TABLE V-continued

Zones of Inhibition (mm)

| CATHETER GROUP | Rifampin Resistant S. epidermidis | Minocycline Passaged s. epidermidis | Minocycline and Rifampin Resistant S. epidermidis |
|---|---|---|---|
| 5% Triclosan + 3% Rifampin | 15 | >25 | >25 |
| 5% Triclosan + 3% Minocycline | 23 | 23 | 24 |

Discussion. The foregoing results suggest that minocycline plus antiseptic is a preferred combination for use in medical devices, as bacterial resistance does not appear to develop and sufficient amounts can be incorporated into catheters to provide long-term activity. In addition, minocycline is highly effective against *S. epidermidis*, one of the major causative organisms of catheter-related infection.

5.5 Example

Superior Results of Antibiotic Plus Antiseptic

Methods. Polyurethane catheters were treated with one of the following solutions:

(1) 3 percent (w/v) chlorhexidine diacetate ("CHA") and 0.75 percent (w/v) silver sulfadiazine ("AgSD") in a solvent consisting of 70 percent (v/v) tetrahydrofuran and 30 percent (v/v) methanol and 3 percent (w/v) 60D polyurethane and 1 percent (w/v) 93A polyurethane;

(2) 3 percent (w/v) minocycline and 3 percent (w/v) rifampin in a solvent consisting of 50 percent (v/v) tetrahydrofuran and 50 percent (v/v) methanol and 3 percent (w/v) 60D polyurethane and 1 percent (w/v) 93A polyurethane;

(3) 3 percent (w/v) chlorhexidine diacetate, 2 percent (w/v) minocycline and 1 percent (w/v) silver sulfadiazine in a solvent consisting of 50 percent (v/v) tetrahydrofuran and 50 percent (v/v) methanol and 3 percent (w/v) 60D polyurethane and 1 percent (w/v) 93A polyurethane;

(4) 5 percent (w/v) triclosan, 1 percent (w/v) silver carbonate ($Ag_2CO_3$), and 1 percent (w/v) citric acid in a solvent consisting of 70 percent (v/v) tetrahydrofuran and 30 percent (v/v) methanol and 3 percent (w/v) 60D polyurethane and 1 percent (w/v) 93A polyurethane;

(5) 5 percent (w/v) triclosan, 3 percent (w/v) minocycline, and 1 percent (w/v) silver carbonate ($Ag_2CO_3$) in a solvent consisting of 50 percent (v/v) tetrahydrofuran and 50 percent (v/v) methanol and 3 percent (w/v) 60D polyurethane and 1 percent (w/v) 93A polyurethane;

(6) 6 percent (w/v) chlorhexidine diacetate in a solvent consisting of 70 percent (v/v) tetrahydrofuran and 30 percent (v/v) methanol and 3 percent (w/v) 60D polyurethane and 1 percent (w/v) 93A polyurethane;

(7) 6 percent (w/v) chlorhexidine diacetate and 1 percent (w/v) silver sulfadiazine in a solvent consisting of 70 percent (v/v) tetrahydrofuran and 30 percent (v/v) methanol and 3 percent (w/v) 60D polyurethane and 1 percent (w/v) 93A polyurethane;

(8) 8 percent (w/v) triclosan in a solvent consisting of 70 percent (v/v) tetrahydrofuran and 30 percent (v/v) methanol and 3 percent (w/v) 60D polyurethane and 1 percent (w/v) 93A polyurethane;

(9) 8 percent (w/v) minocycline in a solvent consisting of 50 percent (v/v) tetrahydrofuran and 50 percent (v/v) methanol and 3 percent (w/v) 60D polyurethane and 1 percent (w/v) 93A polyurethane; or

(10) 1 percent (w/v) silver carbonate ($Ag_2CO_3$) in a solvent consisting of 70 percent (v/v) tetrahydrofuran and 30 percent (v/v) methanol and 3 percent (w/v) 60D polyurethane and 1 percent (w/v) 93A polyurethane.

Catheters were treated by dipping the catheter in the treatment solution for 2–5 seconds and then drying for 24 hours at room temperature. The treated catheters were then cut into segments and tested for their ability to produce zones of inhibition in trypticase soy agar plates seeded with 0.3 mls of cultures of $10^8$ CFU/ml of either *S. epidermidis, Pseudomonas aeruginosa*, or *Enterobacter aerogenes*. Zones of inhibition were measured after 24 hours.

Results. The results of the foregoing experiments are depicted in Table VI.

TABLE VI

Zones of Inhibition (mm)

| GROUP # | TREATMENT | S. epidermidis | P. aeruginosa | E. aerogenes |
|---|---|---|---|---|
| 1 | 3% CHA + 0.75% AgSD | 16 | 11 | 11 |
| 2 | 3% Minocycline + 3% Rifampin | 20 | 0 | 15 |
| 3 | 3% CHA + 2% Minocycline + 1% AgSD | 22 | 15 | 15 |
| 4 | 5% Triclosan + 1% $Ag_2CO_3$ | 20 | 10 | 12 |
| 5 | 5% Triclosan + 1% $Ag_2CO_3$ + 1% Citric Acid | 21 | 11 | 12 |
| 6 | 5% Triclosan + 3% Minocycline + 1% $Ag_2CO_3$ | 25 | 13 | 20 |
| 7 | 6% CHA | 15.5 | 13 | 11 |
| 8 | 6% CHA + 1% AgSD | 16 | 13 | 13 |
| 9 | 8% Triclosan | 15 | 0 | 11 |
| 10 | 8% Minocycline | 20 | 0 | 9 |
| 11 | 1% $Ag_2CO_3$ | 10 | 6 | — |

Conclusions. Catheters treated with one or more antiseptics in combination antibiotic produce larger zones of inhibition than those treated with single agents.

5.6 Example

Anti-adherence Effects of Antibiotic+Antiseptic

Methods. Polyurethane catheters were treated with one of the following solutions:

3 percent (w/v) chlorhexidine diacetate ("CHA") and 0.75 percent (w/v) silver sulfadiazine ("AgSD") in 70 percent (v/v) THF and 30 percent (v/v) methanol with 3 percent (w/v) 60D polyurethane and 1 percent (w/v) 93A polyurethane;

3 percent (w/v) minocycline and 3 percent (w/v) rifampin in 50 percent (v/v) methanol and 50 percent (v/v) THF with 3 percent (w/v) 60D polyurethane and 1 percent (w/v) 93A polyurethane;

3 percent (w/v) chlorhexidine diacetate, 2 percent (w/v) minocycline and 0.75 percent (w/v) silver sulfadiazine in 50 percent (v/v) methanol and 50 percent (v/v) THF with 3 percent (w/v) 60D polyurethane and 1 percent (w/v) 93A polyurethane;

5 percent (w/v) triclosan, 1 percent (w/v) silver carbonate (Ag$_2$CO$_3$), and 1 percent (w/v) citric acid in 70 percent (v/v) THF and 30 percent (v/v) methanol with 3 percent (w/v) 60D polyurethane and 1 percent (w/v) 93A polyurethane;

5 percent (w/v) triclosan, 3 percent (w/v) minocycline and 1 percent (w/v) silver carbonate (Ag$_2$CO$_3$) in 50 percent (v/v) methanol and 50 percent (v/v) THF with 3 percent (w/v) 60D polyurethane and 1 percent (w/v) 93A polyurethane; or 4 cm lengths of catheter, treated as above, were inserted into test tubes containing 5 ml of trypticase soy agar, so that approximately 1 cm of catheter protruded outside the agar. Then, 0.2 ml of a 10$^7$ cfu/ml culture of *Staphylococcus aureus* was applied to the top surface of the agar. The tubes were incubated at 37° C. for seven days. The catheters were then removed and bacterial adherence on the outer surface was determined by rolling the catheter on drug inactivating agar plates, which were incubated for 48 hours at 37° C., after which the bacterial colony counts were determined.

Results. As shown in Table VII, bacterial adherence was found to be lower on catheters impregnated with one or more antiseptics and minocycline.

TABLE VII

Bacterial adherence

| ANTIMICROBIAL TREATMENT | CFU/CM (CATHETER) |
|---|---|
| 3% CHA + 0.75% AgSD | 15 |
| 3% Minocycline + 3% Rifampin | 46 |
| 3% CHA + 3% Minocycline + 0.75% AgSD | 0 |
| 5% Triclosan + 1% Ag$_2$CO$_3$ + 1% Citric Acid | 50 |
| 5% Triclosan + 3% Minocycline + 1% Ag$_2$CO$_3$ | 0 |
| CONTROL | 5 × 10$^3$ |

5.7 Example

Minocycline Plus Antiseptic Treated Catheters

Methods. Polyurethane catheters were treated with one of the following solutions:

8 percent (w/v) minocycline in 50 percent (v/v) methanol and 50 (v/v) percent THF with 3 percent (w/v) 60D polyurethane and 1 percent (w/v) 93A polyurethane;

8 percent (w/v) triclosan in 70 percent (v/v) THF and 30 percent (v/v) methanol with 3 percent (w/v) 60D polyurethane and 1 percent (w/v) 93A polyurethane; or 5 percent (w/v) triclosan and 3 percent (w/v) minocylcine in 50 percent (v/v) methanol and 50 (v/v) percent THF with 3 percent (w/v) 60D polyurethane and 1 percent (w/v) 93A polyurethane.

The various catheter segments were then tested for their ability to produce zones of inhibition in bacterial lawns produced by seeding trypticase soy agar plates with 0.3 milliliters of cultures of 10$^8$ CFU/ml of either *Acinetobacter calcoaceticus, Pseudomonas aeruginosa, Enterobacter aerogenes,* or *Staphylococcus epidermidis*. Zones of inhibition were measured after incubating the plates at 37° C. for 24 hours.

Results. As shown in Table VIIIA, the combination of triclosan and minocycline exhibited enhanced activity relative to the concentrations of minocycline or triclosan tested. Since the zones of inhibition against *S. epidermidis* were turbid and therefore could not be measured very accurately, the cidal activity was checked by subculturing a 1 mm$^2$ area from the zone adjacent to the catheter after three daily transfers of the catheter. The results are shown in Table VIIIB. This data shows enhancement of activity of the combination of minocycline and triclosan over and above that of the individual drugs when used alone at the same weight/volume (as opposed to molar) concentration as that of the combination.

TABLE VIIIA

Zones of Inhibition (mm)

| TREATMENT | Acinetobacter | P. aeruginosa | Enterobacter | S. epidermidis |
|---|---|---|---|---|
| 8% Minocycline | 17 | 0 | 9 | 20 |
| 8% Triclosan | 7 | 0 | 11 | 15 |
| 5% Triclosan + 3% Minocycline | 17 | 0 | 18 | >25 |

TABLE VIIIB

Bacteria Recovered From *S. epidermidis* Zone of Inhibition

| TREATMENT | CFU/MM$^2$ |
|---|---|
| 8% Minocycline | 93 |
| 8% Triclosan | 118 |
| 5% Triclosan + 3% Minocycline | 0 |

The data in Table VIIIB indicate that as regards *S. epidermidis,* the combination of triclosan and minocycline was more effective than either single agent treated catheter.

5.8 Example

Activity Against *Pseudomonas Aeruginosa*

Because of the clinical importance of *Pseudomonas aeruginosa* in catheter-based infections, and because data shown in Table VIIIA failed to show antimicrobial activity against *P. aeruginosa*, experiments were performed testing the effectiveness of other antiseptics, used in conjunction with minocycline, against this organism.

Polyurethane catheters were treated with one of the following solutions:

2 percent (w/v) bismuth nitrate in 50 percent (v/v) methanol and 50 (v/v) percent THF with 3 percent (w/v) 60D polyurethane and 1 percent (w/v) 93A polyurethane;

5 percent (w/v) minocycline in 50 percent (v/v) methanol and 50 (v/v) percent THF with 3 percent (w/v) 60D polyurethane and 1 percent (w/v) 93A polyurethane;

3 percent (w/v) minocycline and 2 percent (w/v) bismuth nitrate in 50 percent (v/v) methanol and 50 percent (v/v) THF with 3 percent (w/v) 60D polyurethane and 1 percent (w/v) 93A polyurethane;

3 percent (w/v) chlorhexidine diacetate in 70 percent (v/v) THF and 30 percent (v/v) methanol with 3 percent (w/v) 60D polyurethane and 1 percent (w/v) 93A polyurethane;

3 percent (w/v) chlorhexidine diacetate and 3 percent (w/v) minocycline in 50 percent (v/v) methanol and 50 percent (v/v) THF with 3 percent (w/v) 60D polyurethane and 1 percent (w/v) 93A polyurethane;

2 percent (w/v) silver carbonate in 50 percent (v/v) methanol and 50 percent (v/v) THF with 3 percent (w/v) 60D polyurethane and 1 percent (w/v) 93A polyurethane; or 3 percent (w/v) minocycline and 1 percent (w/v) silver carbonate in 50 percent (v/v) methanol and 50 percent (v/v) THF with 3 percent (w/v) 60D polyurethane and 1 percent (w/v) 93A polyurethane.

The treated catheters were then cut into segments and tested for their ability to produce zones of inhibition in a bacterial lawn produced by seeding trypticase soy agar plates with 0.3 mls of a $10^8$ CFU/ml culture of *Pseudomonas aeruginosa*, placing the catheter segments vertically on the seeded plate, and then incubating for 24 hours at 37° C.

The results are depicted in Table IX.

TABLE IX

Zones of Inhibition

| TREATMENT | ZONE OF INHIBITION (mm) |
|---|---|
| 2% Bismuth Nitrate | 0 |
| 5% Minocycline | 0 |
| 3% Minocycline + 2% Bismuth Nitrate | 17 |
| 3% Chlorhexidine Diacetate | 11 |
| 3% Chlorhexidine Diacetate + 3% Minocycline | 10.6 |
| 2% Silver Carbonate | 9.0 |
| 3% Minocycline + 1% Silver Carbonate | 9.0 |

In view of the results depicted in Table IX, which demonstrated enhanced antimicrobial effects of bismuth nitrate and minocycline combinations, salts of zinc and cerium in combination with triclosan and/or minocycline were tested as follows.

Polyurethane catheters were treated with one of the following solutions:

5 percent (w/v) triclosan and 3 percent (w/v) minocycline in 50 percent (v/v) methanol and 50 percent (v/v) THF with 3 percent (w/v) 60D polyurethane and 1 percent (w/v) 93A polyurethane;

5 percent (w/v) triclosan, 3 percent (w/v) minocycline and 1 percent (w/v) silver carbonate in 50 percent (v/v) methanol and 50 percent (v/v) THF with 3 percent (w/v) 60D polyurethane and 1 percent (w/v) 93A polyurethane;

5 percent (w/v) triclosan, 3 percent (w/v) minocycline, and 2 percent (w/v) zinc acetate in 50 percent (v/v) methanol and 50 percent (v/v) THF with 3 percent (w/v) 60D polyurethane and 1 percent (w/v) 93A polyurethane;

5 percent (w/v) triclosan, 3 percent (w/v) minocycline, and 2 percent (w/v) bismuth nitrate in 50 percent (v/v) methanol and 50 percent (v/v) THF with 3 percent (w/v) 60D polyurethane and 1 percent (w/v) 93A polyurethane;

1 percent (w/v) silver carbonate in 70 percent (v/v) THF and 30 percent (v/v) methanol with 3 percent (w/v) 60D polyurethane and 1 percent (w/v) 93A polyurethane;

2 percent (w/v) bismuth nitrate in 50 percent (v/v) methanol and 50 percent (v/v) THF with 3 percent (w/v) 60D polyurethane and 1 percent (w/v) 93A polyurethane;

5 percent (w/v) cerium nitrate in 50 percent (v/v) methanol and 50 percent (v/v) THF with 3 percent (w/v) 60D polyurethane and 1 percent (w/v) 93A polyurethane; or 3 percent (w/v) minocycline and 2.4 percent (w/v) cerium nitrate in 50 percent (v/v) methanol and 50 percent (v/v) THF with 3 percent (w/v) 60D polyurethane and 1 percent (w/v) 93A polyurethane.

The salts were used at concentrations which would provide 0.8 percent (w/v) of the metal in each salt.

The catheters were then cut into segments and tested for their ability to produce zones of inhibition in bacterial or yeast lawns produced, respectively, by 0.3 ml of *P. aeruginosa* or 0.5 ml of *Candida albicans*, both at culture concentrations of $10^8$ CFU/ml. The following results, set forth in Table X, were obtained.

TABLE X

Zones of Inhibition (mm)

| TREATMENT | P. aeruginosa | C. albicans |
|---|---|---|
| 5% Triclosan + 3% Minocycline | 0 | 0 |
| 5% Triclosan + 3% Minocycline + 1% Silver Carbonate | 9 | 0 |
| 5% Triclosan + 3% Minocycline + 2% Zinc Acetate | 0 | 0 |
| 5% Triclosan + 3% Minocycline + 2% Bismuth Nitrate | 15 | 0 |
| 1% Silver Carbonate | 6 | 0 |
| 2% Bismuth Nitrate | 0 | 0 |
| 5% Cerium Nitrate | 0 | 0 |
| 3% Minocycline + 2.4% Cerium Nitrate | 6 | 0 |

5.9 Example

Bismuth and Minocycline Combinations

Polyurethane catheters were treated with one of the following solutions:

2 percent (w/v) bismuth nitrate in 50 percent (v/v) methanol and 50 percent (v/v) THF with 3 percent (w/v) 60D polyurethane and 1 percent (w/v) 93A polyurethane;

3 percent (w/v) minocycline in 50 percent (v/v) methanol and 50 percent (v/v) THF with 3 percent (w/v) 60D polyurethane and 1 percent (w/v) 93A polyurethane; or 2 percent (w/v) bismuth nitrate and 3 percent (w/v) minocycline in 50 percent (v/v) methanol and 50 percent (v/v) THF with 3 percent (w/v) 60D polyurethane and 1 percent (w/v) 93A polyurethane.

The various catheter segments were then tested for their ability to produce zones of inhibition in bacterial lawns produced by seeding trypticase soy agar plates with 0.3 mls of cultures of $10^8$ CFU/ml of *Staphylococcus epidermidis*, *Pseudomonas aeruginosa*, *Acinetobacter calcoaceticus*, or *Enterobacter aerogenes*. Zones of inhibition were measured after culturing the plates at 37° C. for 24 hours. The results are shown in Table XI.

TABLE XI

Zones of Inhibition (mm)

| TREATMENT | S. epidermidis | P. aeruginosa | Acinetobacter | Enterobacter |
|---|---|---|---|---|
| 2% Bismuth Nitrate | 6 | 0 | 0 | 0 |
| 3% Minocycline | 23 | 0 | 15 | 11 |
| 2% Bismuth Nitrate + 3% Minocycline | >25 | 17 | 17 | 18 |

In order to further improve the antimicrobial spectrum of non-chlorhexidine groups the following combinations were evaluated. Polyurethane catheters were treated with one of the following solutions:

3 percent (w/v) minocycline and 2 percent (w/v) bismuth nitrate in 50 percent (v/v) methanol and 50 percent (v/v) THF with 3 percent (w/v) 60D polyurethane and 1 percent (w/v) 93A polyurethane;

5 percent (w/v) triclosan in 70 percent (v/v) THF and 30 percent (v/v) methanol with 3 percent (w/v) 60D polyurethane and 1 percent (w/v) 93A polyurethane;

3 percent (w/v) minocycline, 2 percent (w/v) bismuth nitrate, and 5 percent (w/v) triclosan in 50 percent (v/v) methanol and 50 percent (v/v) THF with 3 percent (w/v) 60D polyurethane and 1 percent (w/v) 93A polyurethane;

0.5 percent (w/v) benzalkonium chloride ("BZK") in 70 percent (v/v) THF and 30 percent (v/v) methanol with 3 percent (w/v) 60D polyurethane and 1 percent (w/v) 93A polyurethane; or 3 percent (w/v) minocycline, 2 percent (w/v) bismuth nitrate, and 0.5 percent (w/v) benzalkonium chloride in 50 percent (v/v) methanol and 50 percent (v/v) THF with 3 percent (w/v) 60D polyurethane and 1 percent (w/v) 93A polyurethane.

The ability of treated catheters to produce zones of inhibition was tested as set forth previously in this section, except that the yeast *Candida albicans* was also added to the test panel, the yeast lawn having been produced using 0.5 ml of a culture of $10^8$ CFU/ml. The results are set forth in Table XII.

TABLE XII

| TREATMENT | Zones of Inhibition (mm) | | | | |
|---|---|---|---|---|---|
| | S. epidermidis | P. aeruginosa | Acinetobacter | Enterobacter | C. albicans |
| 3% Minocycline + 2% Bismuth Nitrate | >25 | 17 | 17 | 16 | 0 |
| 5% Triclosan | 12 | 0 | 5 | 7 | 0 |
| 3% Minocycline + 2% Bismuth Nitrate + 5% Triclosan | >25 | 17 | 23 | 19 | 0 |
| 0.5% BZK | 17 | 0 | 6 | 6 | 10 |
| 3% Minocycline + 2% Bismuth Nitrate + 0.5% BZK | >25 | 17 | 20 | 18 | 12 |

The foregoing results show that the use of triclosan with bismuth salt and minocycline enhanced the antimicrobial activity against Enterobacter and Acinetobacter, both of which are associated with catheter-related infections. Use of BZK with bismuth salt and minocycline improved the antimicrobial spectrum to include *C. albicans*. Of the groups tested, all except the 5% triclosan treatment groups exhibited good activity against *S. epidermidis*.

5.10 Example

BZK, Minocycline and Bismuth Salt

Polyurethane catheters were treated with one of the following solutions:

0.5 percent (w/v) benzalkonium chloride ("BZK") in 50 percent (v/v) methanol and 50 percent (v/v) THF with 3 percent (w/v) 60D polyurethane and 1 percent (w/v) 93A polyurethane;

0.5 percent (w/v) benzalkonium chloride and 2 percent (w/v) bismuth nitrate in 50 percent (v/v) methanol and 50 percent (v/v) THF with 3 percent (w/v) 60D polyurethane and 1 percent (w/v) 93A polyurethane;

3 percent (w/v) minocycline and 2 percent (w/v) bismuth nitrate in 50 percent (v/v) methanol and 50 percent (v/v) THF with 3 percent (w/v) 60D polyurethane and 1 percent (w/v) 93A polyurethane;

0.5 percent (w/v) benzalkonium chloride and 3 percent (w/v) minocycline in 50 percent (v/v) methanol and 50 percent (v/v) THF with 3 percent (w/v) 60D polyurethane and 1 percent (w/v) 93A polyurethane;

0.5 percent (w/v) benzalkonium chloride, 2 percent (w/v) bismuth nitrate, and 3 percent (w/v) minocycline in 50 percent (v/v) methanol and 50 percent (v/v) THF with 3 percent (w/v) 60D polyurethane and 1 percent (w/v) 93A polyurethane;

5 percent (w/v) triclosan in 70 percent (v/v) THF and 30 percent (v/v) methanol with 3 percent (w/v) 60D polyurethane and 1 percent (w/v) 93A polyurethane;

3 percent (w/v) minocycline, 2 percent (w/v) bismuth nitrate and 5 percent (w/v) triclosan in 50 percent (v/v) methanol and 50 percent (v/v) THF with 3 percent (w/v) 60D polyurethane and 1 percent (w/v) 93A polyurethane; and, as CONTROL, untreated catheters.

The treated catheters were then dried, cut into segments and used to produce zones of inhibition on lawns of *S. epidermidis* produced by seeding trypticase soy agar plates with 0.3 mls of a $10^8$ CFU/ml culture, and then incubating the seeded plates, with the catheter segments vertically placed, for 24 hours at 37° C.

The zones of inhibition were found to be too large to be accurately measurable, so that a one square millimeter area from within the zone of inhibition was subcultured on an antibiotic free plate. The results are shown in Table XIII. Use of triclosan or BZK was found to enhance the cidal activity of bismuth salt and minocycline.

TABLE XIII

RECOVERED BACTERIA FROM ZONES OF INHIBITION

| TREATMENT | CFU/mm$^2$ |
|---|---|
| 0.5% BZK | 100 |
| 0.5% BZK + 2% Bismuth nitrate | 90 |
| 3% Minocycline + 2% Bismuth nitrate | 200 |
| 0.5% BZK + 3% Minocycline | 100 |
| 0.5% BZK + 2% Bismuth nitrate + 3% Minocycline | 2.5 |
| 5% Triclosan | 150 |
| 3% Minocycline + 2% Bismuth nitrate + 5% Triclosan | 65 |
| CONTROL | $10^4$ |

5.11 Example

Antimicrobial/Antiseptic Combinations

Polyurethane catheters were treated with one of the following solutions.

- 2 percent (w/v) bismuth nitrate in 50 percent (v/v) methanol and 50 percent (v/v) THF with 3 percent (w/v) 60D polyurethane and 1 percent (w/v) 93A polyurethane;
- 5 percent (w/v) triclosan and 3 percent (w/v) minocycline in 50 percent (v/v) methanol and 50 percent (v/v) THF with 3 percent (w/v) 60D polyurethane and 1 percent (w/v) 93A polyurethane;
- 2 percent (w/v) bismuth nitrate and 3 percent (w/v) minocycline in 50 percent (v/v) methanol and 50 percent (v/v) THF with 3 percent (w/v) 60D polyurethane and 1 percent (w/v) 93A polyurethane;
- 2 percent (w/v) bismuth nitrate and 3 percent (w/v) rifampin in 50 percent (v/v) methanol and 50 percent (v/v) THF with 3 percent (w/v) 60D polyurethane and 1 percent (w/v) 93A polyurethane;
- 2 percent (w/v) bismuth nitrate, 3 percent (w/v) minocycline, and 5 percent (w/v) triclosan with 3 percent (w/v) 60D polyurethane and 1 percent (w/v) 93A polyurethane;
- 2 percent (w/v) bismuth nitrate, 3 percent (w/v) rifampin, and 5 percent (w/v) triclosan in 50 percent (v/v) methanol and 50 percent (v/v) THF with 3 percent (w/v) 60D polyurethane and 1 percent (w/v) 93A polyurethane;
- 2 percent (w/v) bismuth nitrate, 3 percent (w/v) minocycline, and 0.5 percent (w/v) benzalkonium chloride in 50 percent (v/v) methanol and 50 percent (v/v) THF with 3 percent (w/v) 60D polyurethane and 1 percent (w/v) 93A polyurethane;
- 5 percent (w/v) triclosan and 2 percent (w/v) bismuth nitrate in 50 percent (v/v) methanol and 50 percent (v/v) THF with 3 percent (w/v) 60D polyurethane and 1 percent (w/v) 93A polyurethane;
- 2 percent (w/v) bismuth nitrate and 0.5 percent (w/v) benzalkonium chloride in 50 percent (v/v) methanol and 50 percent (v/v) THF with 3 percent (w/v) 60D polyurethane and 1 percent (w/v) 93A polyurethane;
- 5 percent (w/v) triclosan, 3 percent (w/v) minocycline, and 1 percent (w/v) silver carbonate in 50 percent (v/v) methanol and 50 percent (v/v) THF with 3 percent (w/v) 60D polyurethane and 1 percent (w/v) 93A polyurethane;
- 3 percent (w/v) minocycline and 1 percent (w/v) silver carbonate in 50 percent (v/v) methanol and 50 percent (v/v) THF with 3 percent (w/v) 60D polyurethane and 1 percent (w/v) 93A polyurethane;
- 5 percent (w/v) minocycline in 50 percent (v/v) methanol and 50 percent (v/v) THF with 3 percent (w/v) 60D polyurethane and 1 percent (w/v) 93A polyurethane;
- 5 percent (w/v) rifampin in 50 percent (v/v) methanol and 50 percent (v/v) THF with 3 percent (w/v) 60D polyurethane and 1 percent (w/v) 93A polyurethane; or
- 0.5 percent (w/v) benzalkonium chloride in 50 percent (v/v) methanol and 50 percent (v/v) THF with 3 percent (w/v) 60D polyurethane and 1 percent (w/v) 93A polyurethane.

The various catheter segments were then tested for their ability to produce zones of inhibition in bacterial lawns produced by seeding trypticase soy agar plates with 0.3 mls of cultures of $10^8$ CFU/ml of *Staphylococcus epidermidis, Pseudomonas aeruginosa, Acinetobacter calcoaceticus, Enterobacter aerogenes,* or *Candida albicans*. Zones of inhibition were measured after culturing the plates at 37° C. for 24 hours. The results are shown in Table XIV.

The data indicates that the combination of bismuth nitrate and an antibiotic, either minocycline or rifampin, showed enhanced activity against *P. aeruginosa*. The combination of minocylcine and bismuth salt appeared to have superior activity, in this regard, than the combination of rifampin and bismuth salt. The combination of bismuth nitrate and minocycline also exhibited enhanced activity against Acinetobacter and Enterobacter bacteria. The addition of benzalkonium chloride to this combination increased antimicrobial activity against *C. albicans* and Acinetobacter. Further, the combination of benzalkonium chloride, minocycline, and bismuth salt was found to exhibit broad spectrum antimicrobial activity.

TABLE XIV

| | Zones of Inhibition (mm) | | | | |
| --- | --- | --- | --- | --- | --- |
| TREATMENT | *P. aeruginosa* | Acinetobacter | *S. epidermidis* | *C. albicans* | Enterobacter |
| 2% Bismuth nitrate | 0 | 0 | 0 | 0 | 0 |
| 5% Triclosan + 3% Minocycline | 0 | 15 | 20 | 0 | 12.5 |
| 2% Bismuth nitrate + 3% Minocycline | 15 | 17 | >25 | 0 | 17 |
| 2% Bismuth nitrate + 3% Rifampin | 11 | 18 | >25 | 0 | — |
| 2% Bismuth nitrate + 3% Minocycline + 5% Triclosan | 17 | 21 | >25 | 0 | 17 |
| 2% Bismuth nitrate + 3% Rifampin + 5% Triclosan | 9 | 16 | >25 | 0 | — |
| 2% Bismuth nitrate + 3% Minocycline + 0.5% BZK | 17 | 20 | 25 | 12 | 16 |

TABLE XIV-continued

Zones of Inhibition (mm)

| TREATMENT | P. aeruginosa | Acinetobacter | S. epidermidis | C. albicans | Enterobacter |
|---|---|---|---|---|---|
| 5% Triclosan + 2% Bismuth nitrate | 0 | 5 | 17 | 0 | — |
| 2% Bismuth nitrate + 0.5% BZK | 0 | 7 | 15 | 10 | — |
| 5% Triclosan + 3% Minocycline + 1% $Ag_2CO_3$ | 6 | 15 | 21 | 0 | 18 |
| 3% Minocycline + 1% $Ag_2CO_3$ | 8 | 14 | 24 | 0 | — |
| 5% Minocycline | 0 | 15 | 20 | 0 | 16 |
| 5% Rifampin | 8 | 15 | 20 | 0 | 16 |
| 0.5% BZK | 0 | 6.5 | 17 | 10 | 6 |

5.12 Example

Combinations of Antibiotics and Bismuth Nitrate

Polyurethane catheters were treated with one of the following solutions:

5 percent (w/v) rifampin in 50 percent (v/v) methanol and 50 percent (v/v) THF with 3 percent (w/v) 60D polyurethane and 1 percent (w/v) 93A polyurethane;

5 percent (w/v) rifampin and 2 percent (w/v)bismuth nitrate in 50 percent (v/v) methanol and 50 percent (v/v) THF with 3 percent (w/v) 60D polyurethane and 1 percent (w/v) 93A polyurethane;

5 percent (w/v) gentamycin in 50 percent (v/v) methanol and 50 percent (v/v) THF with 3 percent (w/v) 60D polyurethane and 1 percent (w/v) 93A polyurethane;

5 percent (w/v) gentamycin and 2 percent (w/v) bismuth nitrate in 50 percent (v/v) methanol and 50 percent (v/v) THF with 3 percent (w/v) 60D polyurethane and 1 percent (w/v) 93A polyurethane;

5 percent (w/v) tobramycin in 50 percent (v/v) methanol and 50 percent (v/v) THF with 3 percent (w/v) 60D polyurethane and 1 percent (w/v) 93A polyurethane;

5 percent (w/v) tobramycin and 2 percent (w/v) bismuth nitrate in 50 percent (v/v) methanol and 50 percent (v/v) THF with 3 percent (w/v) 60D polyurethane and 1 percent (w/v) 93A polyurethane;

5 percent (w/v) ceftazidine in 50 percent (v/v) methanol and 50 percent (v/v) THF with 3 percent (w/v) 60D polyurethane and 1 percent (w/v) 93A polyurethane;

5 percent (w/v) ceftazidine and 2 percent (w/v) bismuth nitrate in 50 percent (v/v) methanol and 50 percent (v/v) THF with 3 percent (w/v) 60D polyurethane and 1 percent (w/v) 93A polyurethane;

5 percent (w/v) dicloxacillin in 50 percent (v/v) methanol and 50 percent (v/v) THF with 3 percent (w/v) 60D polyurethane and 1 percent (w/v) 93A polyurethane;

5 percent (w/v) dicloxacillin and 2 percent (w/v) bismuth nitrate in 50 percent (v/v) methanol and 50 percent (v/v) THF with 3 percent (w/v) 60D polyurethane and 1 percent (w/v) 93A polyurethane;

5 percent (w/v) norfloxacin in 50 percent (v/v) methanol and 50 percent (v/v) THF with 3 percent (w/v) 60D polyurethane and 1 percent (w/v) 93A polyurethane;

5 percent (w/v) norfloxacin and 2 percent (w/v) bismuth nitrate in 50 percent (v/v) methanol and 50 percent (v/v) THF with 3 percent (w/v) 60D polyurethane and 1 percent (w/v) 93A polyurethane;

5 percent (w/v) minocycline in 50 percent (v/v) methanol and 50 percent (v/v) THF with 3 percent (w/v) 60D polyurethane and 1 percent (w/v) 93A polyurethane;

5 percent (w/v) minocycline and 2 percent (w/v) bismuth nitrate in 50 percent (v/v) methanol and 50 percent (v/v) THF with 3 percent (w/v) 60D polyurethane and 1 percent (w/v) 93A polyurethane;

5 percent (w/v) bacitracin in 50 percent (v/v) methanol and 50 percent (v/v) THF with 3 percent (w/v) 60D polyurethane and 1 percent (w/v) 93A polyurethane;

5 percent (w/v) bacitracin and 2 percent (w/v) bismuth nitrate in 50 percent (v/v) methanol and 50 percent (v/v) THF with 3 percent (w/v) 60D polyurethane and 1 percent (w/v) 93A polyurethane;

5 percent (w/v) miconazole in 50 percent (v/v) methanol and 50 percent (v/v) THF with 3 percent (w/v) 60D polyurethane and 1 percent (w/v) 93A polyurethane;

5 percent (w/v) miconazole and 2 percent (w/v) bismuth nitrate in 50 percent (v/v) methanol and 50 percent (v/v) THF with 3 percent (w/v) 60D polyurethane and 1 percent (w/v) 93A polyurethane; or 3 percent (w/v) bismuth nitrate in 50 percent (v/v) methanol and 50 percent (v/v) THF with 3 percent (w/v) 60D polyurethane and 1 percent (w/v) 93A polyurethane.

The various catheter segments were then tested for their ability to produce zones of inhibition in bacterial lawns produced by seeding trypticase soy agar plates with cultures of 0.3 ml of a culture of $10^8$ CFU/ml of Pseudomonas aeruginosa. Catheter segments were placed vertically on the seeded plates, which were then incubated at 37° C. for 24 hours, after which the zones of inhibition of bacterial growth were measured.

The results are shown in Table XV.

TABLE XV

Zones of Inhibition Against Pseudomonas aeruginosa (mm)

| ANTIBIOTIC | TREATMENT*: 5% ANTIBIOTIC | TREATMENT: 5% ANTIBIOTIC + 2% BISMUTH NITRATE |
|---|---|---|
| Rifampin | 8.0 | 11 |
| Gentamycin | 22 | 21 |
| Tobramycin | 27 | 23 |

TABLE XV-continued

Zones of Inhibition Against *Pseudomonas aeruginosa* (mm)

| ANTIBIOTIC | TREATMENT*: 5% ANTIBIOTIC | TREATMENT: 5% ANTIBIOTIC + 2% BISMUTH NITRATE |
|---|---|---|
| Ceftazidine | 28 | 27 |
| Dicloxacillin | 0 | 0 |
| Norfloxacin | 25 | 24 |
| Minocycline | 0 | 15 |
| Bacitracin | 0 | 0 |
| Miconazole | 0 | 0 |
| 3% Bismuth Nitrate | 0 | |

*except for 3% Bismuth Nitrate treated catheter 5.13 Example

Various Bismuth Salt/Minocycline Combinations

Polyurethane catheters were treated with one of the following solutions:

2 percent (w/v) bismuth nitrate in 50 percent (v/v) methanol and 50 percent (v/v) THF with 3 percent (w/v) 60D polyurethane and 1 percent (w/v) 93A polyurethane;

2 percent (w/v) bismuth nitrate and 3 percent (w/v) minocycline in 50 percent (v/v) methanol and 50 percent (v/v) THF with 3 percent (w/v) 60D polyurethane and 1 percent (w/v) 93A polyurethane;

2 percent (w/v) bismuth acetate in 50 percent (v/v) methanol and 50 percent (v/v) THF with 3 percent (w/v) 60D polyurethane and 1 percent (w/v) 93A polyurethane;

2 percent (w/v) bismuth acetate and 3 percent (w/v) minocycline in 50 percent (v/v) methanol and 50 percent (v/v) THF with 3 percent (w/v) 60D polyurethane and 1 percent (w/v) 93A polyurethane;

2 percent (w/v) bismuth citrate in 50 percent (v/v) methanol and 50 percent (v/v) THF with 3 percent (w/v) 60D polyurethane and 1 percent (w/v) 93A polyurethane;

2 percent (w/v) bismuth citrate and 3 percent (w/v) minocycline in 50 percent (v/v) methanol and 50 percent (v/v) THF with 3 percent (w/v) 60D polyurethane and 1 percent (w/v) 93A polyurethane;

2 percent (w/v) bismuth salicylate in 50 percent (v/v) methanol and 50 percent (v/v) THF with 3 percent (w/v) 60D polyurethane and 1 percent (w/v) 93A polyurethane;

2 percent (w/v) bismuth salicylate and 3 percent (w/v) minocycline in 50 percent (v/v) methanol and 50 percent (v/v) THF with 3 percent (w/v) 60D polyurethane and 1 percent (w/v) 93A polyurethane;

2 percent (w/v) bismuth borate in 50 percent (v/v) methanol and 50 percent (v/v) THF with 3 percent (w/v) 60D polyurethane and 1 percent (w/v) 93A polyurethane;

2 percent (w/v) bismuth borate and 3 percent (w/v) minocycline in 50 percent (v/v) methanol and 50 percent (v/v) THF with 3 percent (w/v) 60D polyurethane and 1 percent (w/v) 93A polyurethane;

2 percent (w/v) bismuth mandelate in 50 percent (v/v) methanol and 50 percent (v/v) THF with 3 percent (w/v) 60D polyurethane and 1 percent (w/v) 93A polyurethane;

2 percent (w/v) bismuth mandelate and 3 percent (w/v) minocycline in 50 percent (v/v) methanol and 50 percent (v/v) THF with 3 percent (w/v) 60D polyurethane and 1 percent (w/v) 93A polyurethane;

2 percent (w/v) bismuth palmitate in 50 percent (v/v) methanol and 50 percent (v/v) THF with 3 percent (w/v) 60D polyurethane and 1 percent (w/v) 93A polyurethane;

2 percent (w/v) bismuth palmitate and 3 percent (w/v) minocycline in 50 percent (v/v) methanol and 50 percent (v/v) THF with 3 percent (w/v) 60D polyurethane and 1 percent (w/v) 93A polyurethane;

2 percent (w/v) bismuth benzoate in 50 percent (v/v) methanol and 50 percent (v/v) THF with 3 percent (w/v) 60D polyurethane and 1 percent (w/v) 93A polyurethane;

2 percent (w/v) bismuth benzoate and 3 percent (w/v) minocycline in 50 percent (v/v) methanol and 50 percent (v/v) THF with 3 percent (w/v) 60D polyurethane and 1 percent (w/v) 93A polyurethane;

2 percent (w/v) bismuth sulfadiazine in 50 percent (v/v) methanol and 50 percent (v/v) THF with 3 percent (w/v) 60D polyurethane and 1 percent (w/v) 93A polyurethane;

2 percent (w/v) bismuth sulfadiazine and 3 percent (w/v) minocycline in 50 percent (v/v) methanol and 50 percent (v/v) THF with 3 percent (w/v) 60D polyurethane and 1 percent (w/v) 93A polyurethane; or 5 percent (w/v) minocycline in 50 percent (v/v) methanol and 50 percent (v/v) THF with 3 percent (w/v) 60D polyurethane and 1 percent (w/v) 93A polyurethane.

The various catheter segments were then tested for their ability to produce zones of inhibition in bacterial lawns produced by seeding trypticase soy agar plates with 0.3 ml of a culture of $10^8$ CFU/ml of *Pseudomonas aeruginosa*. Catheter segments were placed vertically on the seeded plates, which were then incubated at 37° C. for 24 hours, after which the zones of inhibition of bacterial growth were measured.

The results are shown in Table XVI, and demonstrate that minocycline enhances the anti-Pseudomonas activity of bismuth salts.

TABLE XVI

Zones of Inhibition Against *Pseudomonas aeruginosa* (mm)

| Bismuth Salt | 2% Bismuth Salt | 2% Bismuth Salt + 3% Minocycline |
|---|---|---|
| Bismuth Nitrate | 0 | 15 |
| Bismuth acetate | 0 | 17 |
| Bismuth citrate | 0 | 17 |
| Bismuth salicylate | 0 | 17 |
| Bismuth borate | 0 | 13 |
| Bismuth mandelate | 0 | 18.5 |
| Bismuth palmitate | 0 | 18.5 |
| Bismuth benzoate | 0 | 18 |
| Bismuth sulfadiazine | 6.5 | 15.5 |

5.14 Example

Broad-spectrum Antimicrobial Activity

Polyurethane catheters were treated with one of the following solutions:

5 percent (w/v) triclosan and 3 percent (w/v) minocycline in 50 percent (v/v) methanol and 50 percent (v/v) THF with 3 percent (w/v) 60D polyurethane and 1 percent (w/v) 93A polyurethane;

5 percent (w/v) triclosan, 3 percent (w/v) minocycline, and 1 percent (w/v) silver carbonate in 50 percent (v/v) methanol and 50 percent (v/v) THF with 3 percent (w/v) 60D polyurethane and 1 percent (w/v) 93A polyurethane;

5 percent (w/v) triclosan, 3 percent (w/v) minocycline, and 0.5% (w/v) benzalkonium chloride ("BZK") in 50 percent (v/v) methanol and 50 percent (v/v) THF with 3 percent (w/v) 60D polyurethane and 1 percent (w/v) 93A polyurethane;

3 percent (w/v) chlorhexidine free base and 3 percent (w/v) minocycline in 50 percent (v/v) methanol and 50 percent (v/v) THF with 3 percent (w/v) 60D polyurethane and 1 percent (w/v) 93A polyurethane;

3 percent (w/v) chlorhexidine free base, 3 percent (w/v) minocycline and 1 percent (w/v) silver carbonate in 50 percent (v/v) methanol and 50 percent (v/v) THF with 3 percent (w/v) 60D polyurethane and 1 percent (w/v) 93A polyurethane;

3 percent (w/v) chlorhexidine free base, 2 percent (w/v) triclosan and 2 percent (w/v) minocycline in 50 percent (v/v) methanol and 50 percent (v/v) THF with 3 percent (w/v) 60D polyurethane and 1 percent (w/v) 93A polyurethane;

0.5 percent (w/v) benzalkonium chloride, 3 percent (w/v) minocycline and 2 percent (w/v) bismuth nitrate in 50 percent (v/v) methanol and 50 percent (v/v) THF with 3 percent (w/v) 60D polyurethane and 1 percent (w/v) 93A polyurethane; or 6 percent (w/v) chlorhexidine diacetate in 70 percent (v/v) THF and 30 percent (v/v) methanol with 3 percent (w/v) 60D polyurethane and 1 percent (w/v) 93A polyurethane.

The various catheter segments were then tested for their ability to produce zones of inhibition in bacterial lawns produced by seeding trypticase soy agar plates with 0.3 mls of cultures of $10^8$ CFU/ml of *Pseudomonas aeruginosa, Acinetobacter calcoaceticus, Staphylococcus epidermidis,* or *Candida albicans*. Zones of inhibition were measured after culturing the plates at 37° C. for 24 hours. The results are shown in Table XVII.

TABLE XVII

| TREATMENT | Zones of Inhibition (mm) | | | |
|---|---|---|---|---|
| | P. aeruginosa | Acineto- bacter | S. epi- dermidis | C. albicans |
| 5% Triclosan + 3% Minocycline | 0 | 15 | 22 | 0 |
| 5% Triclosan + 3% Minocycline + 1% Silver Carbonate | 6 | 15 | 22 | 0 |
| 5% Triclosan + 3% Minocycline + 0.5% BZK | 0 | 15 | 21 | 7 |
| 3% CHX free base + 3% Minocycline | 11 | 12 | 22 | 8 |
| 3% CHX free base + 3% Minocycline + 1% Silver Carbonate | 12 | 12 | 22 | 10 |
| 3% CHX free base + 2% Triclosan + 2% Minocycline | 11 | 13 | 22 | 8 |
| 0.5% BZK + 3% Minocycline + 2% Bismuth Nitrate | 15 | 20 | 25 | 12 |
| 6% CHA | 10 | 11 | 15 | 9 |

Various publications are cited herein, the contents of which are hereby incorporated in their entireties.

We claim:

1. An anti-infective medical article prepared by exposing a polymer-containing medical article, for an effective period of time, to a treatment solution comprising between 1 and 8 percent (weight/volume) of minocycline and between 1 and 8 percent (weight/volume) of a chlorhexidine compound selected from the group consisting of chlorhexidine free base and chlorhexidine diacetate.

2. The anti-infective medical article of claim 1, where the treatment solution further comprises bismuth nitrate at a concentration of between 0.5 and 2.0 percent (weight/volume).

3. The anti-infective medical article of claim 1, where the treatment solution further comprises between 0.2 and 1.0 percent (weight/volume) benzalkonium chloride.

4. The anti-infective medical article of claim 2, where the treatment solution further comprises between about 0.25 and 1.0 percent (weight/volume) benzalkonium chloride.

5. An anti-infective medical article prepared by exposing a polymer-containing medical article, for an effective period of time, to a treatment solution comprising between 1 and 8 percent (weight/volume) of minocycline, between 1 and 8 percent (weight/volume) of triclosan, and bismuth nitrate at a concentration of between 0.5 and 2.0 percent (weight/volume).

6. The anti-infective medical article of claim 5, where the treatment solution further comprises between 0.25 and 1.0 percent (weight/volume) benzalkonium chloride.

7. An anti-infective medical article prepared by exposing a polymer-containing medical article, for an effective period of time, to a treatment solution comprising between 1 and 8 percent (weight/volume) of minocycline, between 0.25 and 1.0 percent (weight/volume) of benzalkonium chloride, and between 0.5 and 2.0 percent (weight/volume) of bismuth nitrate.

8. An intravascular catheter comprising between 100 and 450 micrograms of minocycline per centimeter and between 130 and 520 micrograms of a chlorhexidine compound selected from the group consisting of chlorhexidine free base and chlorhexidine diacetate.

9. The catheter of claim 8 further comprising between 50 and 300 micrograms per centimeter of bismuth nitrate.

10. The catheter of claim 9 further comprising between 25 and 100 micrograms per centimeter of benzalkonium chloride.

11. The catheter of claim 8 further comprising between 25 and 300 micrograms per centimeter of a silver-containing compound selected from the group consisting of silver sulfadiazine and silver carbonate.

12. An intravascular catheter comprising between 100 and 450 micrograms of minocycline per centimeter, between 130 and 750 micrograms of triclosan per centimeter, and between 50 and 300 micrograms of bismuth nitrate per centimeter.

13. The catheter of claim 12 further comprising between 25 and 100 micrograms per centimeter of benzalkonium chloride.

14. The catheter of claim 12 further comprising between 25 and 300 micrograms per centimeter of silver carbonate.

15. An antiinfective medical article prepared by exposing a polymer-containing medical article for an effective period of time to a treatment solution comprising between 1 and 8 percent (weight/volume) of minocycline and between 0.5 and 2.0 percent (weight/volume) of bismuth nitrate.

* * * * *

UNITED STATES PATENT AND TRADEMARK OFFICE
CERTIFICATE OF CORRECTION

PATENT NO. : 6,582,719 B2
DATED : June 24, 2003
INVENTOR(S) : Modak et al.

It is certified that error appears in the above-identified patent and that said Letters Patent is hereby corrected as shown below:

Title page,
Item [57], ABSTRACT,
Line 2, "antiseptic" should read -- antiseptics --

Column 1,
Line 36, "antibiotic" should read -- antibiotics --
Line 47, "gram negative" should read -- gram-negative --
Line 49, "ameoba" should read -- amoeba --

Column 2,
Line 1, "gram negative" should read -- gram-negative --

Column 3,
Line 15, "hexane)." should read -- hexane. --
Line 34, "napthoate" should read -- naphthoate --

Column 5,
Line 9, "contains" (second occurrence) should be deleted

Column 8,
Table IIB, "Inoculumn" should read -- Inoculum --

Column 12,
Line 14, "mls" should read -- ml --

Column 13,
Table VII, "CFU/CM" should read -- cfu/cm --
Line 50, "minocylcine" should read -- minocycline --
Line 58, "CFU/ml" should read -- cfu/ml --

Column 14,
Table VIIIB, "CFU/MM$^2$" should read -- cfu/mm$^2$ --

Column 15,
Line 10, "mls" should read -- ml --; and "CFU/ml" should read -- cfu/ml --

Column 16,
Line 6, "CFU/ml." should read -- cfu/ml. --
Line 42, "mls" should read -- ml --
Line 43, "CFU/ml" should read -- cfu/ml --

Column 17,
Line 22, "CFU/ml." should read -- cfu/ml. --

UNITED STATES PATENT AND TRADEMARK OFFICE
CERTIFICATE OF CORRECTION

PATENT NO. : 6,582,719 B2
DATED : June 24, 2003
INVENTOR(S) : Modak et al.

It is certified that error appears in the above-identified patent and that said Letters Patent is hereby corrected as shown below:

Column 18,
Line 43, "mls" should read -- ml --; and "CFU/ml" should read -- cfu/ml --

Column 20,
Line 22, "mls" should read -- ml --
Line 23, "CFU/ml" should read -- cfu/ml --
Line 31, "minocylcine" should read -- minocycline --

Column 21,
Lines 48 and 51, "ceftazidine" should read -- ceftazidime --

Column 22,
Line 51, "CFU/ml" should read -- cfu/ml --

Column 23,
Table XV, "Ceftazidine" should read -- Ceftazidime --

Column 24,
Line 34, "CFU/ml" should read -- cfu/ml --

Column 25,
Line 35, "mls" should read -- ml --
Line 36, "CFU/ml" should read -- cfu/ml --

Column 26,
Line 60, "antiinfective" should read -- anti-infective --
Line 61, "article for" should read -- article, for --
Line 62, "time to" should read -- time, to --

Signed and Sealed this

Third Day of February, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,582,719 B2
DATED : June 24, 2003
INVENTOR(S) : Modak et al.

It is certified that error appears in the above-identified patent and that said Letters Patent is hereby corrected as shown below:

Title page,
Item [*] Notice, should read -- Subject to any disclaimer, the term of this patent is extended or adjusted under 35 U.S.C. 154 (b) by 213 days. --

Signed and Sealed this

Twenty-eighth Day of September, 2004

JON W. DUDAS
*Director of the United States Patent and Trademark Office*